(12) United States Patent
Barr

(10) Patent No.: US 11,426,099 B2
(45) Date of Patent: Aug. 30, 2022

(54) MOBILE DEVICE AVATAR GENERATION FOR BIOFEEDBACK TO CUSTOMIZE MOVEMENT CONTROL

(71) Applicant: Ready 2 Perform Technology LLC, Calabasas, CA (US)

(72) Inventor: Andrew Barr, Calabasas, CA (US)

(73) Assignee: Ready 2 Perform Technology LLC, Calabasas, CA (US)

( * ) Notice: Subject to any disclaimer, the term of this patent is extended or adjusted under 35 U.S.C. 154(b) by 330 days.

(21) Appl. No.: 16/837,300

(22) Filed: Apr. 1, 2020

(65) Prior Publication Data

US 2021/0307650 A1 Oct. 7, 2021

(51) Int. Cl.
| | |
|---|---|
| *A61B 5/11* | (2006.01) |
| *G06K 9/00* | (2022.01) |
| *G06V 40/20* | (2022.01) |
| *G06T 7/20* | (2017.01) |
| *G06V 20/20* | (2022.01) |
| *G16H 20/30* | (2018.01) |
| *G06F 3/01* | (2006.01) |

(52) U.S. Cl.
CPC ............ *A61B 5/1121* (2013.01); *A61B 5/1116* (2013.01); *A61B 5/1128* (2013.01); *G06F 3/011* (2013.01); *G06T 7/20* (2013.01); *G06V 20/20* (2022.01); *G06V 40/20* (2022.01); *G06V 40/23* (2022.01); *G16H 20/30* (2018.01); *G06T 2207/30196* (2013.01)

(58) Field of Classification Search
None
See application file for complete search history.

(56) References Cited

U.S. PATENT DOCUMENTS

| | | | | |
|---|---|---|---|---|
| 2012/0277891 | A1* | 11/2012 | Aragones | G09B 19/003 700/91 |
| 2013/0120445 | A1* | 5/2013 | Shimomura | G02B 27/017 345/629 |
| 2015/0099252 | A1* | 4/2015 | Anderson | G06T 7/251 434/257 |
| 2016/0182802 | A1 | 6/2016 | Bone et al. | |

(Continued)

OTHER PUBLICATIONS

Horwitz, Jeremy, "Vicon's Capture.U Adds Live AR Tracking Using Apple's ARKIT," Mar. 10, 2020, https://venturebeat.com/2020/03/10/vicons-capture-u-adds-live-ar-athletic-tracking-using-apples-arkit/.

*Primary Examiner* — Sean P Dougherty
*Assistant Examiner* — Benjamin S Melhus
(74) *Attorney, Agent, or Firm* — Patent Ingenuity, P.C.; Samuel K. Simpson

(57) ABSTRACT

A system has a sensor that senses baseline sensor data corresponding to one or more baseline movements of a user and senses dynamic sensor data corresponding to one or more dynamic movements of the user. The dynamic sensor data is captured after the baseline sensor data. Furthermore, the system has an image capture device integrated within a mobile computing device. The image capture device captures baseline image capture data corresponding to the one or more baseline movements of the user and captures dynamic image capture data corresponding to the one or more dynamic movements of the user. The dynamic image capture data is captured after the baseline image capture data. Additionally, the mobile computing device is in operable communication with the sensor.

18 Claims, 13 Drawing Sheets

(56) References Cited

U.S. PATENT DOCUMENTS

2016/0367857 A1* 12/2016 Aragones ............. A61B 5/6831
2017/0266502 A1*  9/2017 Aragones ........... A63B 24/0062
2018/0226146 A1*  8/2018 Aragones ............... G16H 20/60
2019/0224528 A1*  7/2019 Omid-Zohoor ...... A61B 5/0024

* cited by examiner

| Biomechanical Assessment | Variable | Baseline Range | Biomechanical Rule |
|---|---|---|---|
| General Strength | Max Force | a to b | (a - Rule Factor) to (b - Rule Factor) |
| Force Absorption | Impact Force | c to d | (c - Rule Factor) to (d - Rule Factor) |
| Reactive Strength | Ground Contact Time | e to f | (e - Rule Factor) to (f - Rule Factor) |
| Total Body Power | Jump Distance | g to h | (g - Rule Factor) to (h - Rule Factor) |
| Movement | Peak Torso extension/flexion | i to j | (i - Rule Factor) to (j - Rule Factor) |
| Manual Mobility | Peak shoulder flexion | k to l | (k - Rule Factor) to (l - Rule Factor) |

FIG. 4

MOBILE DEVICE AVATAR GENERATION FOR BIOFEEDBACK TO CUSTOMIZE MOVEMENT CONTROL

BACKGROUND

1. Field

This disclosure generally relates to computing systems. More particularly, the disclosure relates to the field of biomechanical visualization systems.

2. General Background

Sports performance experts (e.g., coaches, trainers, etc.) often attempt to work with athletes to maximize athletic performance for a particular athlete in a specific sport, preempt potential sports-related injuries, and/or rehabilitate the athlete from existing injuries. A common approach is for the sports performance expert to provide an in-person physical assessment of the athlete; yet, such an assessment is often inaccurate. Specifically, the sports performance expert is left guessing various metrics (e.g., fatigue, force production, angular joint articulation) generated by the athlete through various exercises, and then attempts to improve the performance of the athlete based on those estimated metrics. In essence, the sports performance expert performs a subjective assessment, which may not take into account invisible metrics (e.g., fatigue) or metrics that are difficult for a human to capture (e.g., joint articulation angles) with any degree of precision and/or consistency. As a result, the analysis performed by a sports performance expert may be quite subjective, and prone to error.

To alleviate such subjectivity, sports performance experts may employ various types of equipment to measure biomechanical data in a quantitative, rather than qualitative, manner. However, managing data outputted by such equipment is often quite difficult because of the large amount of biomechanical data that may be generated by such equipment. For example, that data has to be analyzed to then generate training reports based on the analysis. To perform the analysis and generate the reports may often take weeks, or possibly even months; such a time delay is often too significant to help minimize injury risk factors that may affect a player in the interim period. Furthermore, even after the foregoing time delay, the resulting report may be error prone because of a misinterpretation of the biomechanical data by the sports performance expert analyzing the biomechanical data during the analysis phase. Accordingly, the performance enhancing, injury prevention, and/or injury rehabilitation exercises prescribed in a report, generated from use of conventional equipment, may lack specificity with respect to the actual biomechanical issue that actually needs to be addressed.

Given the lack of a systematic approach to evaluating biomechanical data, both conventional qualitative and quantitative approaches to sports performance enhancement pose significant concerns. Furthermore, many athletes (e.g., non-professionals such as children) do not have access to a sports performance expert and/or sports performance equipment, leaving many athletes susceptible to significant risk of injury.

SUMMARY

In one embodiment, a system has a sensor that senses baseline sensor data corresponding to one or more baseline movements of a user and senses dynamic sensor data corresponding to one or more dynamic movements of the user. The dynamic sensor data is captured after the baseline sensor data. Furthermore, the system has an image capture device integrated within a mobile computing device. The image capture device captures baseline image capture data corresponding to the one or more baseline movements of the user and captures dynamic image capture data corresponding to the one or more dynamic movements of the user. The dynamic image capture data is captured after the baseline image capture data. Additionally, the mobile computing device is in operable communication with the sensor.

The system also has a processor that is programmed to generate user-specific baseline data based upon the baseline sensor data and the baseline image capture data, generate one or more predetermined biomechanical rules according to the user-specific baseline data, generate a virtual avatar based upon the one or more predetermined biomechanical rules, and generate one or more cues corresponding to the virtual avatar based upon non-compliance of one or more real-world movements of the user with the one or more predetermined rules. The one or more real-world movements are determined from the dynamic sensor data and the dynamic image capture data. The virtual avatar has virtual movements that are synchronized in real-time with the corresponding one or more real-world movements. Finally, the system has a memory device that stores the user-specific baseline data in a baseline data structure for access by the processor.

As an alternative, a computer program may have a computer readable storage device with a computer readable program stored thereon that implements the functionality of the aforementioned system. As yet another alternative, a process that utilizes a processor may implement the functionality of the aforementioned system.

BRIEF DESCRIPTION OF THE DRAWINGS

The above-mentioned features of the present disclosure will become more apparent with reference to the following description taken in conjunction with the accompanying drawings wherein like reference numerals denote like elements and in which:

FIG. 4 illustrates an example of the baseline data structure illustrated in FIG. 1.

DETAILED DESCRIPTION

Figure 1:
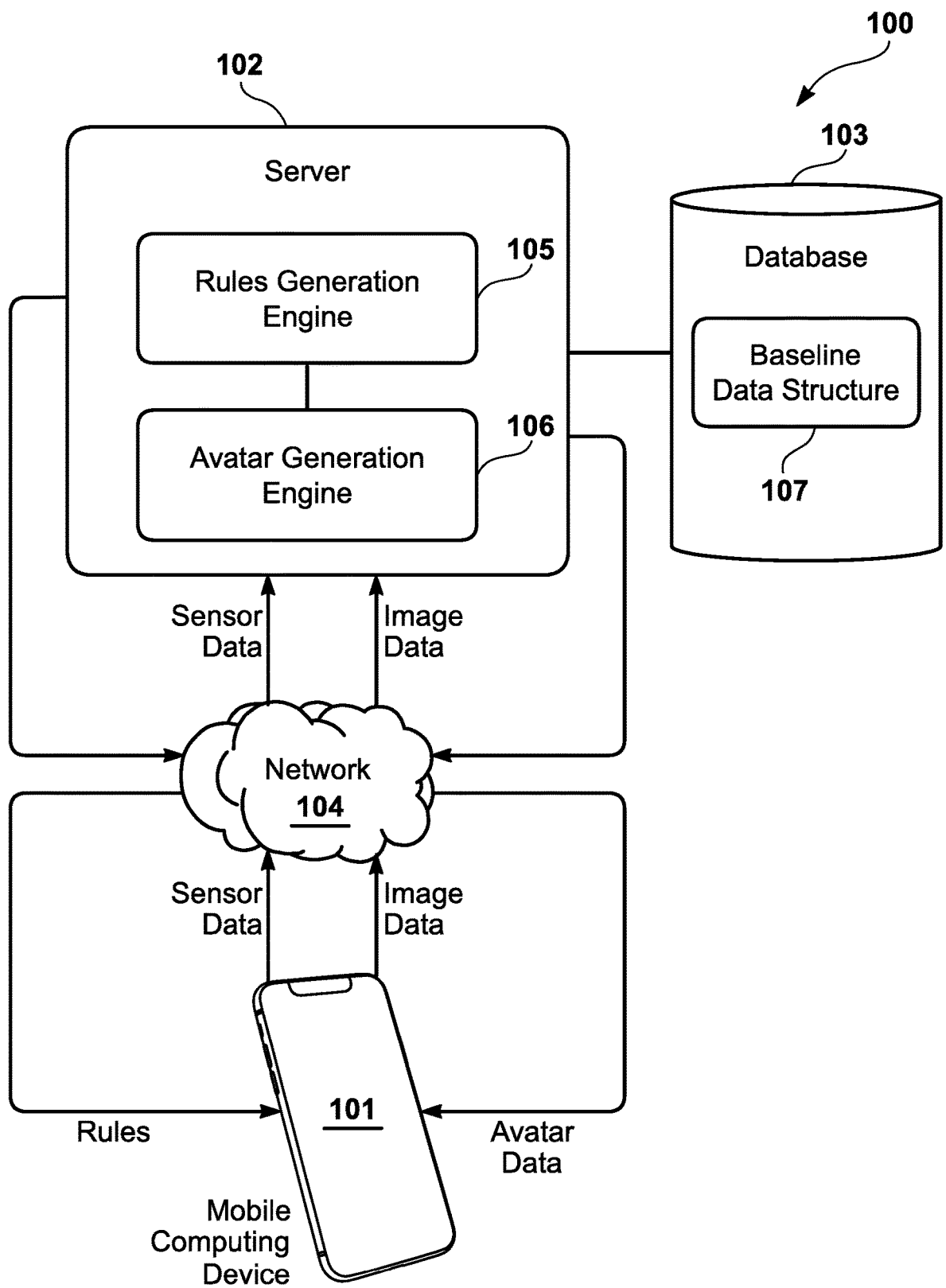
FIG. 1 illustrates an avatar generation system that has a mobile computing device communicating with a server, through a network.

An avatar generation configuration generates a virtual avatar that may provide biofeedback to a user (i.e., mirroring the biomechanical movements of the user). Rather than providing a standardized overlay, indicating universal ranges of motion, the avatar generation configuration generates a customized avatar that uniquely identifies movement control for a particular user. In other words, acceptable ranges of motion may vary from user-to-user—biomechanical efficiency is not one-size-fits-all. In particular, the avatar generation configuration generates a baseline data structure that is generated by a rules generation engine. A user may be prompted, by a mobile computing device (e.g., smartphone, tablet device, smart glasses, smart watch, smart bracelet, smart apparel, etc.) or another user operating the mobile computing device, to perform a series of movements to capture baseline data particular to that user (i.e., the user's movement signature). During this learning phase, the rule generation engine, optionally with an artificial intelligence ("AI") system, determines optimal ranges of movement for the particular user, for which the movement data was captured by the mobile computing device. For example, the mobile computing device may prompt (e.g., audio, video, haptic vibration, etc.) the user, or operator of the mobile computing device capturing video of the user, to perform the various baseline movements. Once the baseline data structure is established, the avatar generation configuration has the customized set of rules from which biomechanical analysis may be performed for the particular user.

In contrast with analyzing static positions (e.g., sitting at a desk) or movements that involve repetitive motions in a stationary position (e.g., squat), the avatar generation configuration is capable of analyzing more complex dynamic movements that are sport-specific (e.g., a basketball jump shot). Based upon the baseline data structure, the avatar generation configuration is able to determine deviations from the biomechanical rules in the baseline data structure, and provide recommendations (e.g., exercises) to correct the dynamic movement for the user, on a customized basis. Furthermore, because the baseline data structure is established prior to actual analysis of the user's dynamic movements, the baseline rules are available for fast access when performing biomechanical analysis of a user performing a particular sport-specific movement, thereby allowing for real-time assessment of a user's dynamic movement and real-time correction of that that dynamic movement.

The real-time correction may be provided via an avatar, corresponding to the user performing the dynamic movement, rendered on the display device. Notably, the avatar generation configuration generates the avatar based on image data of the user, which may be captured by an image capture device integrated within the mobile computing device or a distinct image capture device that is in operable communication with the mobile computing device, in conjunction with sensor data of the user, which may be captured by one or more sensors positioned on the user or in proximity to the user. Furthermore, the avatar generation configuration may analyze the image data to determine kinematic motion along one plane, while analyzing the sensor data to determine kinematic motion along a distinct plane. For example, for the purpose of determining movement control along the transverse plane (e.g., chest movement, sacrum movement, thigh movement, etc.), a sensor may be significantly more accurate than a camera, which is limited in its ability to fully capture movement along the transverse plan when viewing the user along the frontal plane, which is a typical viewpoint from a mobile computing device; conversely, the camera may be more accurate in capturing data along the frontal plane given its direct viewpoint as opposed to computer vision processes utilized in conjunction with one or more sensors to deduce imagery. Accordingly, the avatar generation configuration may obtain imagery data for multiple planes, but filter the image data for the plane that is optimal for an image capture device. Similarly, the avatar generation configuration may obtain sensor data for multiple planes, but filter the sensor data for the plane that is optimal for a sensor. Therefore, the avatar generation configuration selects data from a particular data source (e.g., image capture device, sensor, etc.) based on a particular plane and the data source that is optimal for that plane. As a result, the avatar generation configuration is able to provide for improved accuracy in detecting kinematic motion over conventional configurations.

Furthermore, the avatar generation configuration may provide biomechanical feedback to the user via the avatar. For example, if the user should correct a particular movement of a limb, the GUI of the mobile computing device may provide a visual indication on, or in proximity to, the avatar. As a result, the user or an additional user operating the mobile computing device may determine in real-time (measured as a humanly imperceptible time difference between the movement of the user and the generation of the avatar), or substantially real-time (measured as a noticeable time difference that is perceived as an insignificant time lag (e.g., one to five seconds)), biomechanical corrections to the movement of the user during that movement, as rendered by the avatar. If another user views the avatar, that other user can then effectively coach the user performing the movement as to how to correct the biomechanical movement. Conversely, if the user performing the movement views the mobile computing device (e.g., holding the mobile computing device during viewing, wearing the mobile computing device during viewing, positioning the mobile computing device on a tripod, supporting the mobile computing device with an accessory such as a kickstand, etc.), he or she may be able to self-correct the movement during performance of the movement, or shortly thereafter.

Additionally, the GUI rendered at the mobile computing device may provide other resources to assist the user performing the movement with biomechanical correction. For example, the GUI may display a biomechanical assessment particular to the user performing the movement. The biomechanical assessment may be used by performance enhancement coach, a friend, or the user performing the movement to pinpoint specific biomechanical deficiencies for correction. As another example, the GUI may display various instructional videos and/or output various instructional audio emissions for specific exercises that are recommended by the avatar generation configuration, potentially via the AI, to enhance the movement control of the user. For example, the avatar generation configuration may recommend a squat exercise for improving particular kinematic motions associated with a dynamic movement, such as a jump shot. The GUI on the mobile computing device may then provide a video and/or an audio instructional as to how to properly perform the squat. (A squat is just one of many examples of possible exercises that may be recommended, given that many other types of exercises may be recommended to resolve a particular biomechanical deficiency of the user's movement control.)

In one embodiment, the avatar is a two-dimensional ("2-D") or three-dimensional ("3D") representation of the user performing the movement that may be displayed by a mobile computing device. Alternatively, instead of a mobile computing device, a stationary computing device (e.g., desktop computer, kiosk, etc.) may be utilized to render the avatar. In an alternative embodiment, the avatar may be displayed as a hologram that is emitted by a holographic projector in operable communication with a mobile computing device or a stationary computing device.

The avatar generation configuration may be utilized by a wide variety of types of athletes (casual to professional, children to adults, solo sports to team sports, etc.). Rather than necessitating an in-person sports performance expert and a sports performance lab with extensive equipment, the avatar generation configuration may be implemented in a physical environment that is convenient for the user, such as a living room where dynamic movements may be potentially simulated, or a physical environment that provides a realistic feel for a sport-specific event, such as a basketball court. Furthermore, the avatar generation configuration may be utilized for a variety of movements (e.g., exercise, sport-specific movement, sport-specific drill, yoga pose, etc.). Instead of waiting a prolonged period of time for data obtained from sports lab equipment in conventional configurations to measure and analyze data, the avatar generation configuration presents cues to the user in real-time, or substantially real-time, so that the user may immediately make biomechanical corrections when it matters most to maximize performance and/or prevent injury: during performance of the athletic movement.

FIG. 1 illustrates an avatar generation system 100 that has a mobile computing device 101 communicating with a server 102, through a network 104. Firstly, the mobile computing device 101 may be utilized to obtain baseline data customized to the particular movements of a user; via integrated componentry within the mobile computing device 101 or one or more peripheral devices in operable communication therewith. The baseline data may be determined based on sensor data and/or imagery data obtained by the mobile computing device 101. In one embodiment, the mobile computing device 101 sends the sensor data and/or the imagery data through the network 104 to the server 102, which may then utilize a rules generation engine 105 to establish one or baseline rules based on the baseline data. The baseline data may have overlapping data points, the redundancy of which may be removed by the rules generation engine 105. For example, image data and sensor data both may include data pertaining to a user's hips, but the rules generation engine 105 may filter out the image data, which is captured from the perspective of a frontal plane, to only include the sensor data captured from the perspective of a transverse plane, thereby leading to improved accuracy in detecting kinematic motion and improved computing efficiency by eliminating redundancies. For instance, the server 102 may be in operable communication with a database 103 that stores a baseline data structure 107. In essence, the baseline data structure 107 provides for fast and efficient access to one or more predetermined biomechanical rules corresponding to baseline data customized to a particular user. The server 102 may send the biomechanical rules, via the network 104, to the mobile computing device 101, which may then determine, based on real-time sensor data and/or image data, compliance with the one or more predetermined biomechanical rules, which were determined according to previously captured image and/or sensor data. For example, the user performing the movement may have been prompted by the mobile computing device 101, or a user operating the mobile computing device 101, to perform one or more baseline movements, which may be directly or indirectly tied to movement control for a sport-specific movement. For instance, the user may be prompted to perform a squat movement for determining baseline joint angles particular to a user for subsequent performance of the dynamic movement of a jump shot; alternatively, the user may be prompted to perform the actual movement of the jump shot to determine the baseline data for the jump shot. After generation of the rules by the rules generation engine 105, the mobile computing device 101 may determine real-time compliance with the rules based on the sensor data and image data captured by the mobile computing device 101. Furthermore, the mobile computing device 101 may receive avatar data from an avatar generation engine 106 at the server 102. In essence, the avatar is a visual representation specific to the user that has customized dimensions (e.g., limb lengths, widths, etc.) and kinematic ranges particular to the user, as indicated by the rules of the baseline data structure. The avatar may be represented in the form of data, or a program such as an applet that is accessible by the mobile computing device 101 via the server 102. The mobile computing device 101 may operate its own computer executable code, or the applet, to display visual non-compliance indications on the avatar, or in proximity thereto. (Audio indications or haptic vibration indications may be emitted as an alternative to visual indications.) In this embodiment, the mobile computing device 101 relies on the server 102 as a cloud-based configuration to generate the rules and the avatar.

In alternative embodiment, the mobile computing device 101 has the rules generation engine 105, the avatar generation engine 106, and/or the database 103 stored locally thereon, without full reliance on the server 102. In other words, the mobile computing device 101 may communicate with the server 102 in a manner that allows for partial cloud computing.

In essence, the visual or audio indications may be cues that help guide the user performing the movement toward compliance with the biomechanical rules established by the rules generation engine 105. The biomechanical rules are based on specific ranges of motion (e.g., joint angles, anatomical structure flexion, etc.) that are customized for the user performing the movement based on the anatomical structure and ranges of motion particular to that user, rather than just a general set of ranges that may not be conducive to the particular user performing the movement. Furthermore, the biomechanical rules are not only established to account for the maximum ranges of motion of the particular user, but also ranges of motion that are deemed to be safe. In other words, just because a user can move a limb through a particular range of motion does not mean that the user should fully move through that range, or apply force throughout that entire range. As a result, the rules generation engine 105 may apply a rule factor (e.g., amount of range reduction, range multiplier that reduces the range by a certain multiplier, etc.) to the maximum ranges of motion of a particular user to help minimize the risk of injury for that user, while also training the user to obtain peak performance through his or her range of motion for particular limbs and/or joints. Upon detecting a deviation from the predetermined rules (e.g., a deviation from one or more predetermined ranges of motion as determined by a rule factor applied to the ranges of motion corresponding to the anatomical structures of a particular user), which are based on the particular user's baseline data and potential rule factors, the avatar generation configuration 100 may generate the cues to guide the user back toward compliance with the rules. If the avatar generation system 100 determines that the user is incapable of complying with the rules, which may be based on a predetermined time threshold for rule compliance being exceeded, the avatar generation system 100 may generate an interrupt instruction to pause, or temporarily prevent user access to, the rendering of the avatar until the user accesses one or more safety instructional videos or audio recordings.

Figure 2A:
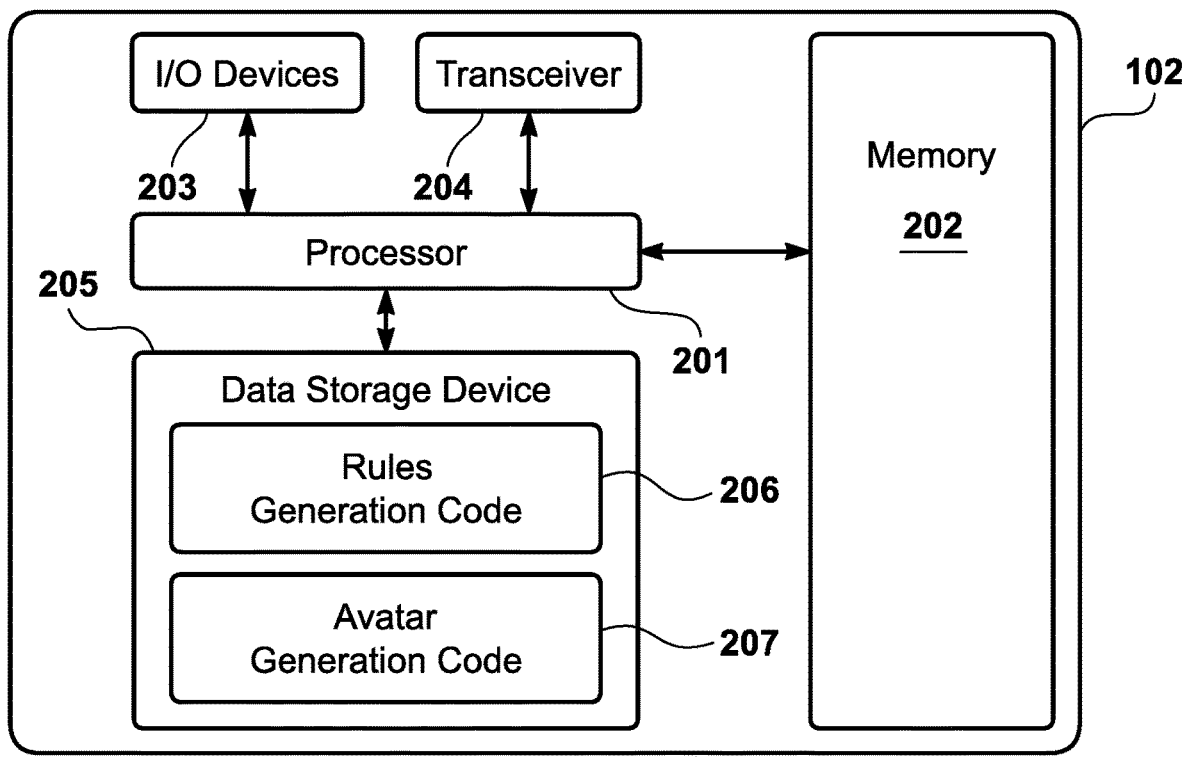
FIG. 2A illustrates a system configuration for the server illustrated in FIG. 1A.
Figure 2B:
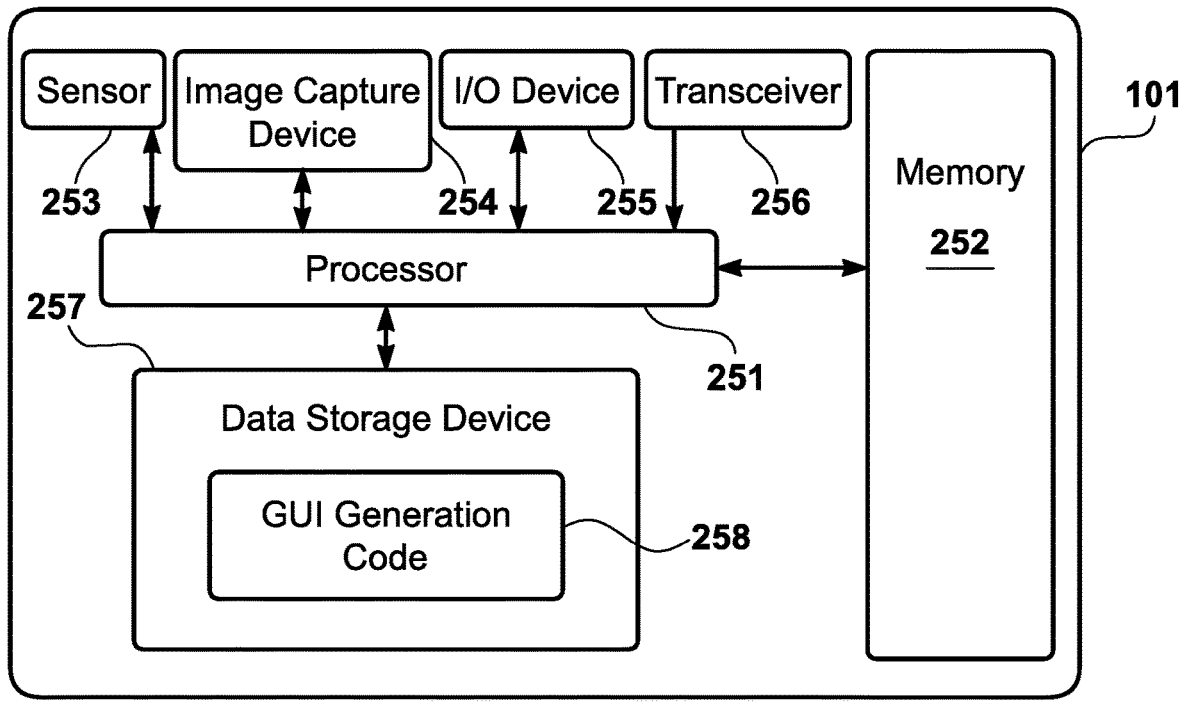
FIG. 2B illustrates a system configuration for the mobile computing device illustrated in FIG. 1A

FIGS. 2A and 2B illustrate system configurations for the various componentry of the avatar generation system 100 illustrated in FIG. 1. In particular, FIG. 2A illustrates a system configuration for the server 102 illustrated in FIG. 1A. The server 102 may have a processor 201, which may be specialized for image analysis, audio analysis, baseline data composition from imagery data and sensor data, and/or avatar generation. Accordingly, the processor 201 may be used to perform the operations illustrated in FIG. 1 for generating an avatar, and potential corresponding cues, based on compliance with one or more predetermined biomechanical rules.

The system configuration may also include a memory device 202, which may temporarily store the baseline data structure 107, illustrated in FIG. 1, for improved processing times by the processor 201. As a result, the avatar generation system 100 is able to provide real-time, or substantially real-time, biomechanical assessment and/or biomechanical cue correction via the avatar. Furthermore, the memory device 202 may store computer readable instructions performed by the processor 201. As an example of such computer readable instructions, a data storage device 205 within the system configuration may store biomechanical rules generation code 206 and avatar generation code 207. The processor 201 may execute the biomechanical rules generation code 206 to establish the biomechanical rules as predetermined rules by compositing sensor and image data into baseline data that is stored in the baseline data structure 107, which may then be stored by the memory device 202 for real-time, or substantially real-time, avatar generation. Additionally, the rules generation code 206 may allow the processor 201 to analyze subsequently received sensor and image data to determine real-time compliance with the predetermined rules. Furthermore, the processor 201 may execute the avatar generation code 207 to automatically generate the avatar, as well as visual and/or audio cues corresponding to the avatar.

Moreover, the system configuration may have one or more input/output ("I/O") devices 203 that may receive inputs and provide outputs. Various devices (e.g., keyboard, microphone, mouse, pointing device, hand controller, joystick, display device, holographic projector, etc.) may be used for the I/O devices 203. The system configuration may also have a transceiver 204 to send and receive data. Alternatively, a separate transmitter and receiver may be used instead.

Conversely, FIG. 2B illustrates a system configuration for the mobile computing device 101 illustrated in FIG. 1A. In particular, a processor 251, which may be specialized for image rendering, may be used to perform rendering of the avatar associated with the user performing the movement, and corresponding virtual cues.

The system configuration may also include a memory device 252, which may temporarily store computer readable instructions performed by the processor 251. As an example of such computer readable instructions, a data storage device 257 within the system configuration may store GUI generation code 258. The processor 251 may execute the GUI generate code 258 to generate and/or render a GUI associated with a software application executed by the mobile computing device 101. The GUI may include an interface that allows for menu selections for biomechanical assessment and biomechanical correction particular to the user performing the movement, as well as real-time, or substantially real-time, visual rendering of an avatar associated with the user during the performance of the movement by the user. In another embodiment, the avatar generation code 207 is stored by the data storage device 257 of the mobile computing device 101 instead of the server 102.

Moreover, the system configuration of the mobile computing device 101 may have sensors 253 integrated therein, or may be in operable communication with the sensors 253. Furthermore, the one or more sensors 253 may be positioned directly on the user to perform various measurements during the user's performance of the movement. For example, the sensors 253 may be inertial measurement units (e.g., accelerometer, gyroscope, magnetometer, etc.) that are utilized to measure movement of various limbs/joints (e.g., knees, ankles, waist, lower back chest, etc.) of the user performing the movement. In essence, the sensors 253 may be utilized to detect subtle movements of the user performing the movement along a particular plane, such as the transverse plane. The processor 201 and/or the processor 251 may utilize various computer vision processes to generate imagery and perform image analysis on the data captured by the sensors 253. Additionally, the system configuration of the mobile computing device 101 may have one or more image capture devices 254 (e.g., camera) integrated therein, or may be in operable communication with the one or more image capture devices 254. In contrast with the sensors 253 that are most suitable for detecting subtle movements along the transverse plane, the image capture devices 254 may be utilized to detect gross motor movements, such as along the frontal plane. As an example, the mobile computing device 101 may have an integrated image capture device 254, but may be in operable communication with one or more external sensors that are positioned directly on the user performing the movement via one or more connection mechanisms (e.g., straps, bands, belts, etc.). In one embodiment, the processor 251 of the mobile computing device 101 sends the sensor and image data to the server 102 so that the server 102 may perform the compositing of the sensor and image data. In another embodiment, the processor 251 of the mobile computing device 101 performs the compositing of the sensor and imagery data.

In another embodiment, an integrated sensor may be used in place of distinct sensors 253 and image capture devices 254. For example, a depth/heat sensing (e.g., thermal imaging) camera may be utilized to capture imagery and sense movement of a limb of the user. Furthermore, the sensors 253 may be specifically configured to detect not only kinematic motion, but also biometric data (e.g., heartrate, temperature, etc.); such biometric data may be indicative of fatigue and/or joint inflammation. Accordingly, the one or more sensors 253 may sense/measure a variety of metrics (e.g., velocity, acceleration, force, heat, etc.), potentially independent of, or in conjunction with, the image capture devices 254.

If external to the mobile computing device 101, the sensors 253 and/or image capture devices 254 may communicate with the mobile computing device 101 via various types of connections (e.g., wired connection or wireless connection such as WiFi, BLUETOOTH, etc.).

Finally, the system configuration of the mobile computing device 101 may receive inputs and provide outputs. Various devices (e.g., keyboard, microphone, mouse, pointing device, hand controller, joystick, display screen, holographic projector, etc.) may be used for the I/O devices 255. If external to the mobile computing device 101, the I/O devices 255 may communicate with the mobile computing device 101 via various types of connections (e.g., wired connection or wireless connection such as WiFi, BLUETOOTH, etc.).

The system configuration may also have a transceiver 256 to send and receive data. Alternatively, a separate transmitter and receiver may be used instead.

Figure 3A:
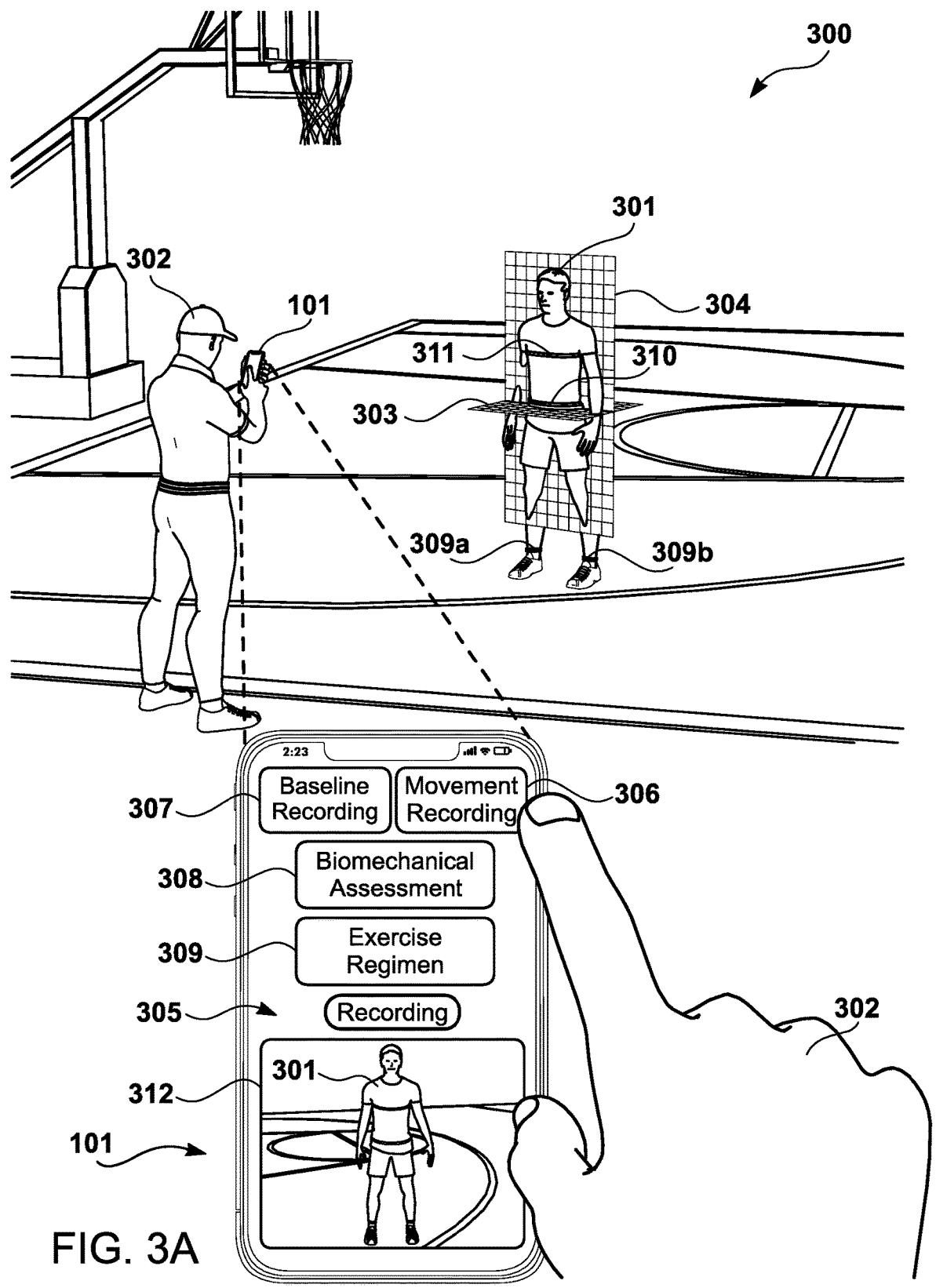
FIG. 3A illustrates an example of a multi-user environment that may be a basketball court in which a first user wants to perform various basketball movements.
Figure 3B:
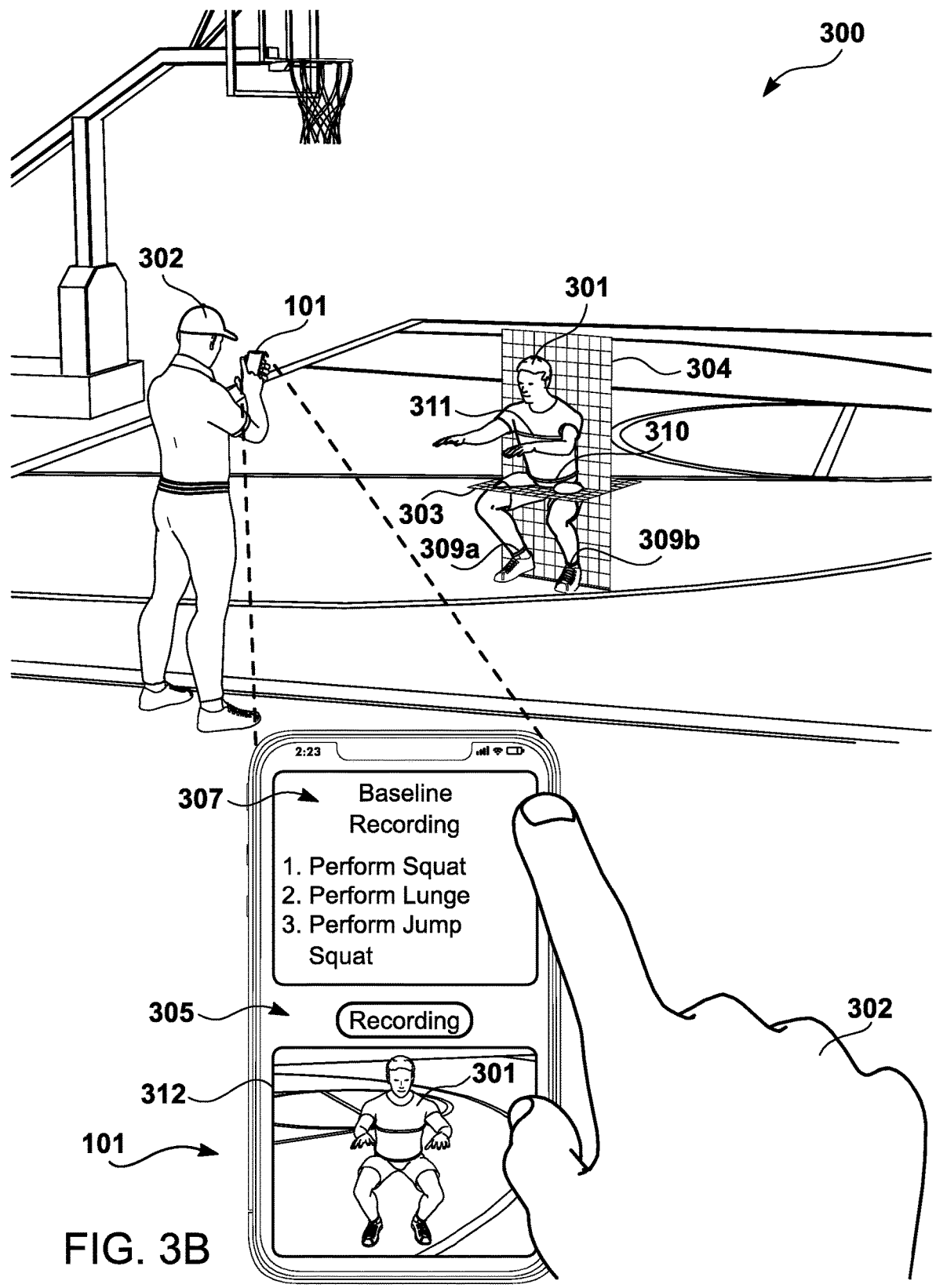
FIG. 3B illustrates a graphical user interface ("GUI") of the mobile computing device visually depicting prompts for the first user to perform the sport-specific exercises, such as a squat.

FIGS. 3A and 3B illustrate a multi-user environment 300 in which the avatar generation system 100 may be practically implemented. As an example, as illustrated in FIG. 3A, the multi-user environment 300 may be a basketball court in which a first user 301 wants to perform various basketball movements. Furthermore, a second user 302 (e.g., friend, coach, trainer, etc.) may operate the mobile computing device 101, illustrated in FIGS. 1 and 2B. The first user 301 may wear a variety of sensors, such as a chest sensor 311, a waist sensor 310, and ankle sensors 309a and b. (These sensors are provided only as examples. Additional, or alternative, sensors may be positioned on other anatomical structures of the first user 301, such as the elbows, wrists, knees, head, etc.) Additionally, the second user 302 may operate an image capture device 254 to capture imagery of the movement of the first user 301.

Although not visible to the users 301 and 302, FIG. 3A illustrates a frontal plane 304 and a transverse plane 303 to depict movements along these different planes; particularly, to illustrate the data filtering specific to a particular plane for optimal accuracy in generating an avatar.

Furthermore, FIG. 3A illustrates the GUI 305 that is generated by the mobile computing device 102. The GUI 305 improves operation of the mobile computing device 102 with respect to biomechanical assessment and correction. Firstly, the GUI 305 renders a baseline recording indicium 307, which allows the second user 302 to obtain baseline data for movements of the first user 301. The first user 301 may be prompted by the mobile computing device 102 to perform one or more baseline movements, such as exercises that determine the baseline ranges of motion for the particular user 301, which may differ significantly from that of another user. After the second user 302 activates the baseline recording indicium 307, the mobile computing device 101 may emit, via visual or audio outputs, one or more prompts to request that the first user 301 perform the movements that will help generate the baseline data. As an example, the first user 301 may want to work on his or her basketball jump shot. Accordingly, the mobile computing device 101 may determine certain sport-specific exercises with ranges of motion that correlate to a basketball jump shot, such as squats and lunges. Therefore, upon receiving prompts from the mobile computing device 101, or prompts received from the second user 302 interacting with the mobile computing device 101, the first user 301 may perform the baseline movements while the second user 302 maneuvers the mobile computing device 101 to capture video of the first user 301 performing the baseline exercises. In one embodiment, the GUI 305 displays a video area 312 that displays real-time, or substantially real-time, recording of the real-world movements of the first user 301.

FIG. 3B illustrates the GUI 305 of the mobile computing device 101 visually depicting prompts for the first user 301 to perform the baseline exercises, such as a squat. In particular, as the first user 301 performs the squat motion, the image capture device 254, integrated within the mobile computing device 101, and the sensors 309a, 309b, 310, and 311, worn by the first user 301, detect kinematic motion along the frontal plane 304 and the transverse plane 303. However, the image capture device 254 is clearly more suited to optimally capture the gross motor movements along the frontal plane 304; whereas the sensors 309a, 309b, 310, and 311 are more suited to capture fine motor movements along the transverse plane 303.

FIG. 4 illustrates an example of the baseline data structure 107 illustrated in FIG. 1. Upon gathering various image and sensor data from the image capture device 254 and the sensors 309a, 309b, 310, and 311, respectively, the server 102 and/or the mobile computing device 101, illustrated in FIG. 1, may composite baseline data for the first user 301. In particular, the server 102 and/or the mobile computing device 101 may select the most optimal data source for a given plane, filter out data from other data sources, and composite the resulting data into a baseline data set that is customized for movement control of the first user 301. The baseline data structure 107 may then store a plurality of biomechanical rules based on the baseline data set.

As an example, the baseline data structure 107 may have a plurality of fields, such as a biomechanical assessment field 401, a variable field 402, a baseline range field 403, and a rules field 404. For instance, the biomechanical assessment field 401 may include various biomechanical assessment metrics (e.g., general strength, force absorption, relative strength, total body power, movement, and manual mobility). Furthermore, for each biomechanical assessment metric, the baseline data structure 107 may store a variable specific to that biomechanical assessment metric (e.g., maximum force for general strength, impact force for force absorption, ground contact time for relative strength, jump distance for total body power, peak torso extensional flexion for movement, and peak shoulder flexion for manual mobility). (Although only one variable is illustrated per biomechanical assessment for illustrative purposes, multiple variables may be stored for each biomechanical assessment metric.)

Furthermore, the baseline data structure 107 may store baseline range data, which is indicated by the baseline range field 403, that indicates one or more predetermined ranges of motion specific to the particular user 301, as determined from the composite baseline data (i.e. optimal sensor data composited with optimal image data). Additionally, the baseline data structure 107 may indicate one or more biomechanical rules that are generated based on the composite baseline data. In one embodiment, the processor 201 of the server 102 and/or the processor 251 of the mobile computing device 101 may generate the biomechanical rules by imposing a rule factor on the composite baseline data. For instance, allowing for full knee flexion throughout the entirety of the predetermined range of motion for a particular user may be considered unsafe for the user 301; whereas reducing the range of motion by a predetermined amount at each endpoint of the range of motion may help preserve the safety of the user 301 and the longevity of his or her limbs and joints. For example, an angular displacement of a knee may allow for a range of motion of one hundred twenty degrees, but a rule may be generated to reduce that range of motion at one end point to only allow for a ninety degree displacement. In certain instances, one endpoint may be reduced by a particular rule factor whereas another endpoint may not be reduced at all.

The baseline data structure 107 may be stored as a variety of data structures (e.g., two-dimensional array as illustrated in FIG. 4, one-dimensional array, linked list, double linked list, etc.). Furthermore, the baseline data structure 107 may have one or more pointers to other data structures, which may also store baseline data.

Figure 5A:
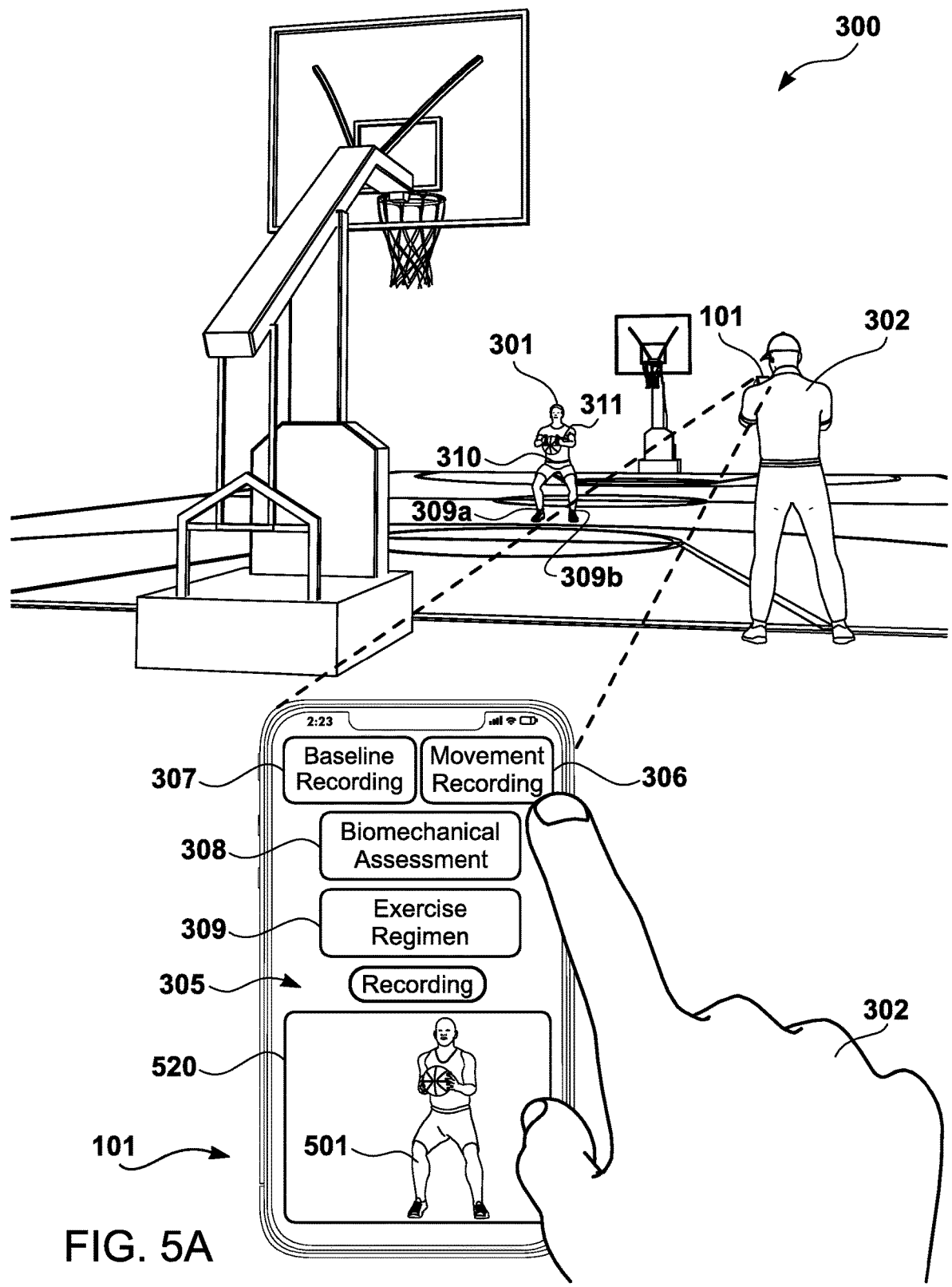
FIG. 5A illustrates the second user selecting, at a GUI rendered by the mobile computing device, the movement recording indicium to begin the process of avatar generation based upon real-time, or substantially real-time, data determined from the kinematic motion of the first user.
Figure 5B:
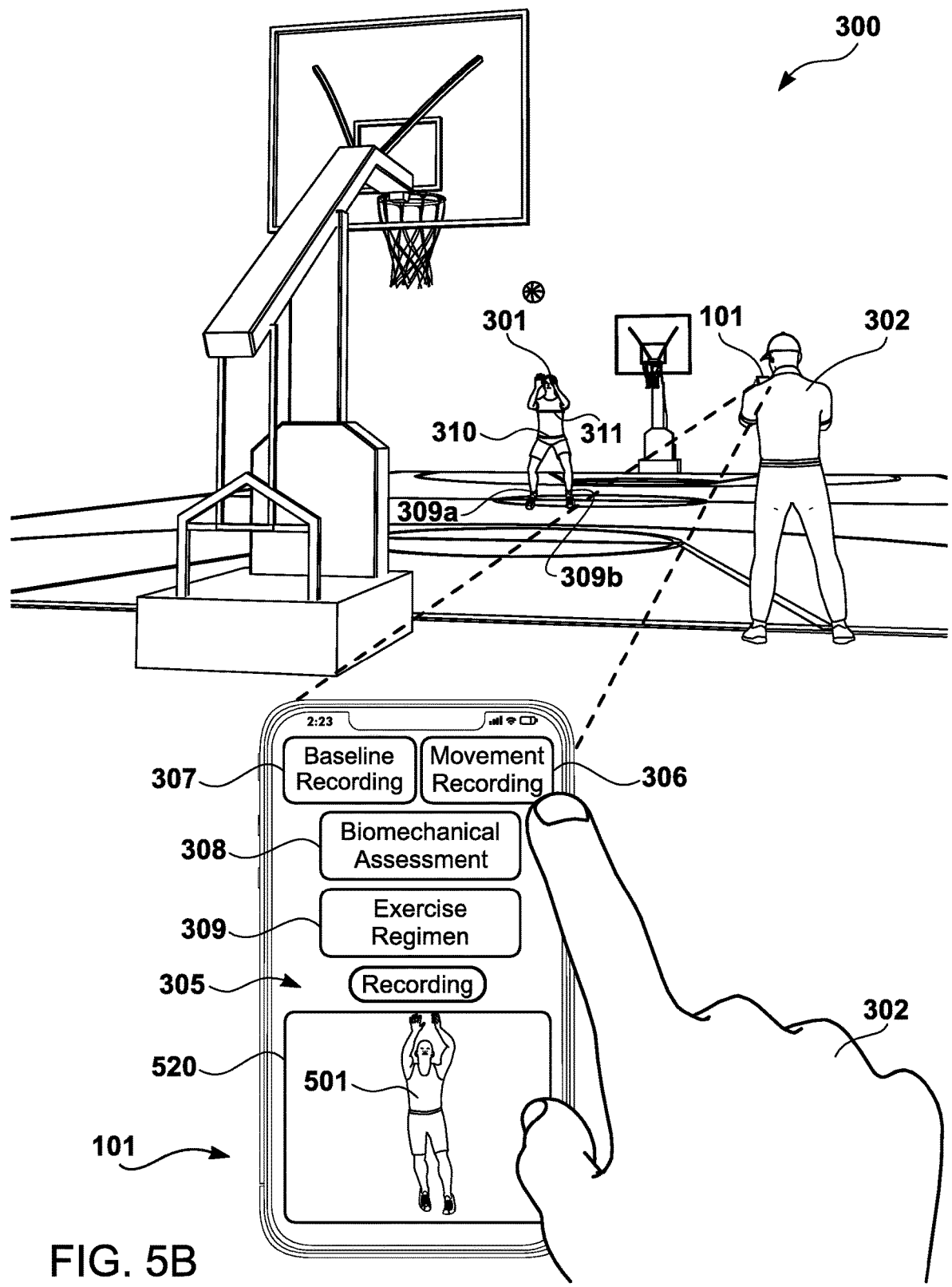
FIG. 5B illustrates an example of the mobile computing device rendering an avatar, which provides biofeedback regarding the movements of the first user in real-time, or substantially real-time, of performance of those movements by the first user.
Figure 5C:
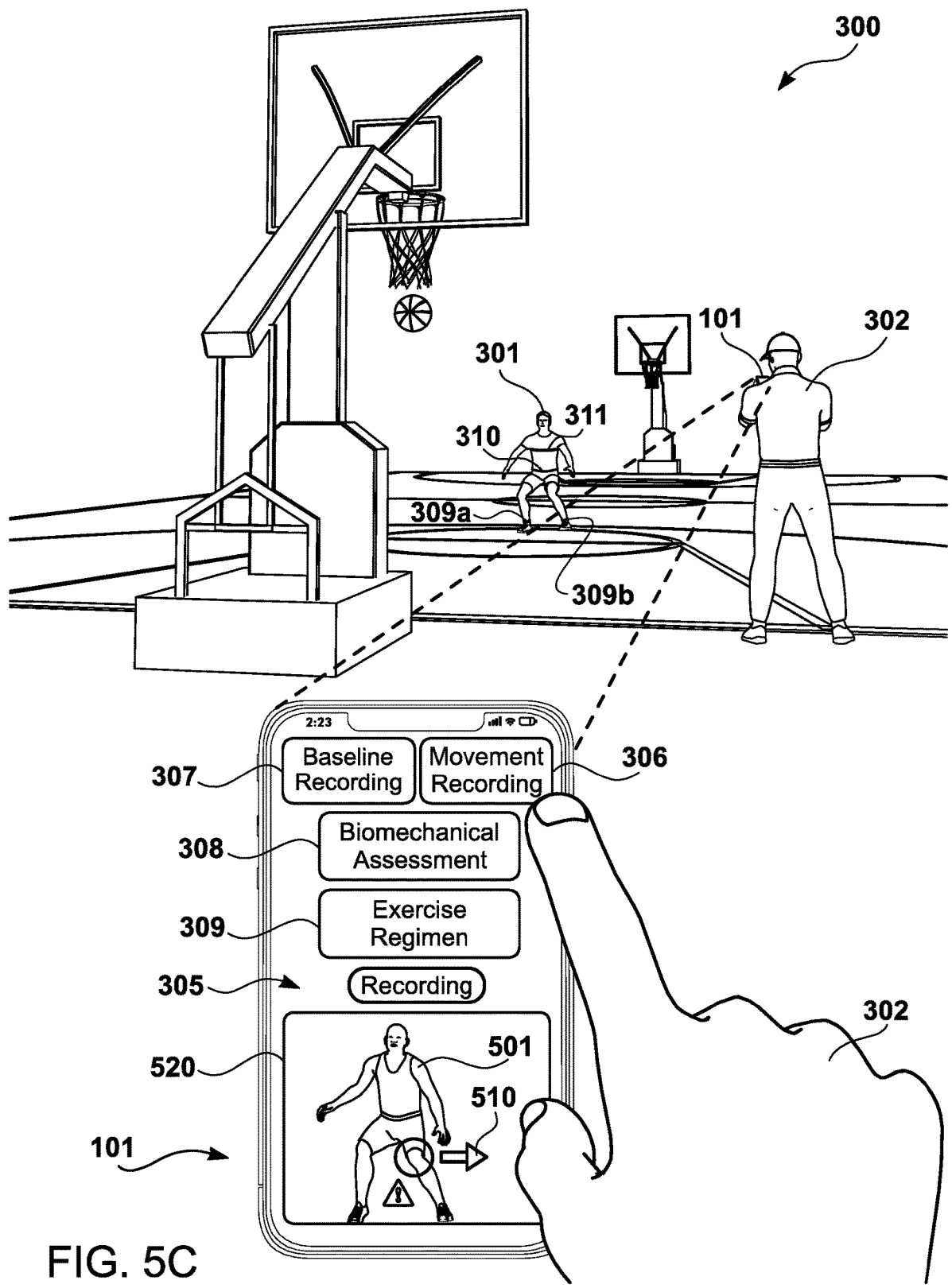
FIG. 5C illustrates an example of the avatar, illustrated in FIG. 5B, concluding a virtual movement that corresponds to a real-world movement of the first user.

FIGS. 5A-5E illustrate an example of avatar generation in a sport-specific environment 300 (e.g., basketball) to provide biofeedback to the first user 301 to customize control movements (e.g., jump shot) particular to that user. For example, FIG. 5A illustrates the second user 302 selecting, at GUI 305 rendered by the mobile computing device 101, the movement recording indicium 306 to begin the process of avatar generation based upon real-time, or substantially real-time, data determined from the kinematic motion of the first user 301. At this point, the mobile computing device 101 may already have the one or more predetermined biomechanical rules, which were based on the composited baseline data that was composited from the senor and image data illustrated in FIGS. 3A and 3B, as an example. Accordingly, after selection of the movement recording indicium 306, the mobile computing device 101 may begin receiving subsequent sensor and image data, potentially in the same manner that was used to capture data for the purpose of generating the one or more predetermined rules. FIG. 5B illustrates an example of the mobile computing device 101 rendering an avatar 501, which provides biofeedback regarding the movements of the first user 301 in real-time, or substantially real-time, of performance of those movements by the first user 301 (i.e., the avatar 501 mirrors the movements of the first user 301 in a synchronized manner). The avatar may be displayed in a virtual video display area 520. As an example, FIG. 5B illustrates the first user 301 beginning to perform a jump shot; concurrently with such movement, the mobile computing device 101 renders a display of the avatar 501 also performing that movement. As a result, the second user 302 is able to view an up-close display of the particular limb/joint motion of the first user 301, thereby providing the second user 302 more detailed biomechanical data than viewing the first user 301 without the mobile computing device 101. Furthermore, FIG. 5C illustrates an example of the avatar 501, illustrated in FIG. 5B, concluding a virtual movement that corresponds to a real-world movement of the first user 301. Moreover, the mobile computing device 101 and/or the server 102 may monitor the biomechanical movements of the first user 301 to determine compliance with the biomechanical rules stored by the baseline data structure 107, illustrated in FIG. 4. The mobile computing device 101 may then display a visual indication 510 (e.g., arrow, marker, flashing light, etc.) and/or emit an audio indication (e.g., voice-based instruction) that indicates how the first user 301 may perform correction of any movements that do not comply the one or more predetermined rules, such as those indicated by the rules field 404 of the baseline data structure 107 illustrated in FIG. 4. For example, the first user 301 may have landed in such a manner that one of his or her knees moved inward too much in a manner that exceeds an acceptable predetermined range of motion, as dictated by the one or more predetermined biomechanical rules. As a result, the mobile computing device 101 may generate a correction visual cue 510 that allows the first user 301 to perform correction in real-time, or substantially real-time, with his or her movement. In essence, the correction visual cue 510 allows for customized biofeedback to customize movement control for the particular first user 301.

Figure 5D:
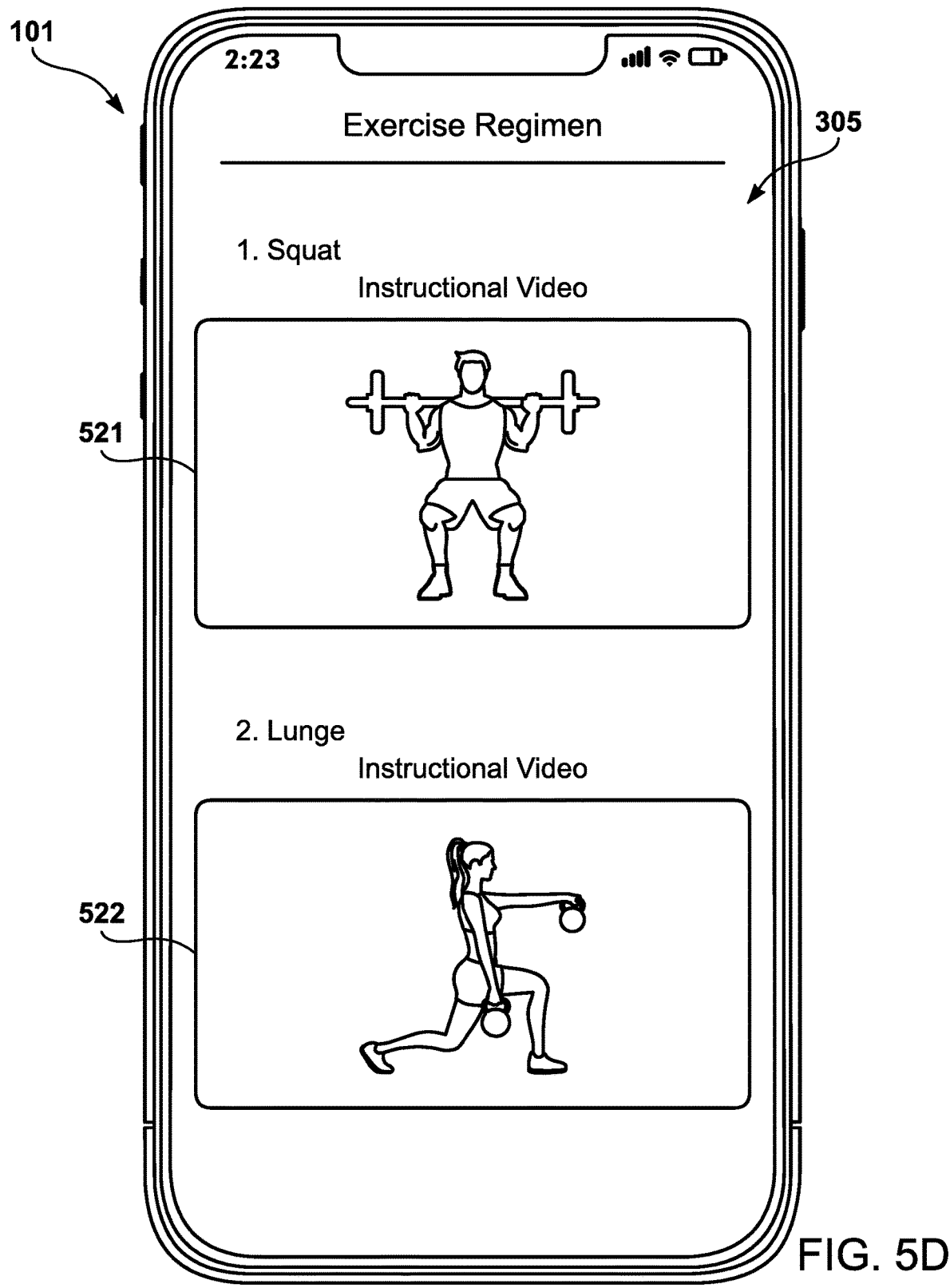
FIG. 5D illustrates the mobile computing device automatically redirecting the GUI to one or more instructional videos upon the correction performed by the first user not complying with the one or more predetermined biomechanical rules.

In one embodiment, as illustrated in FIG. 5D, the mobile computing device 101 may automatically redirect the GUI 305 to one or more instructional videos 521 and 522 upon the correction performed by the first user 301 not complying with the one or more predetermined biomechanical rules. For example, the mobile computing device 101 and/or the server 102 may establish a predetermined time limit in which the first user 301 has to comply with the one or more predetermined rules. Should the first user 301 not complete the correction within that predetermined time limit, the mobile computing device 101 and/or the server 102 may deduce that the first user 301 is having some difficulty (e.g., biomechanical, knowledge, etc.) performing the correction. Accordingly, the mobile computing device 101 and/or the server 102 may automatically redirect the GUI 305 to an exercise regimen screen to allow the user to watch videos and/or listen to audio instructing the first user 301 on exercises to help improve the biomechanical ability of the first user 301 to perform the biomechanical correction. In an alternative, the second user 302 may manually navigate to the exercise regimen display and select from the instructional videos and/or audio. For instance, the second user 302 may select the exercise regimen indicium 309 from the GUI 305 illustrated in FIG. 3A.

Figure 5E:
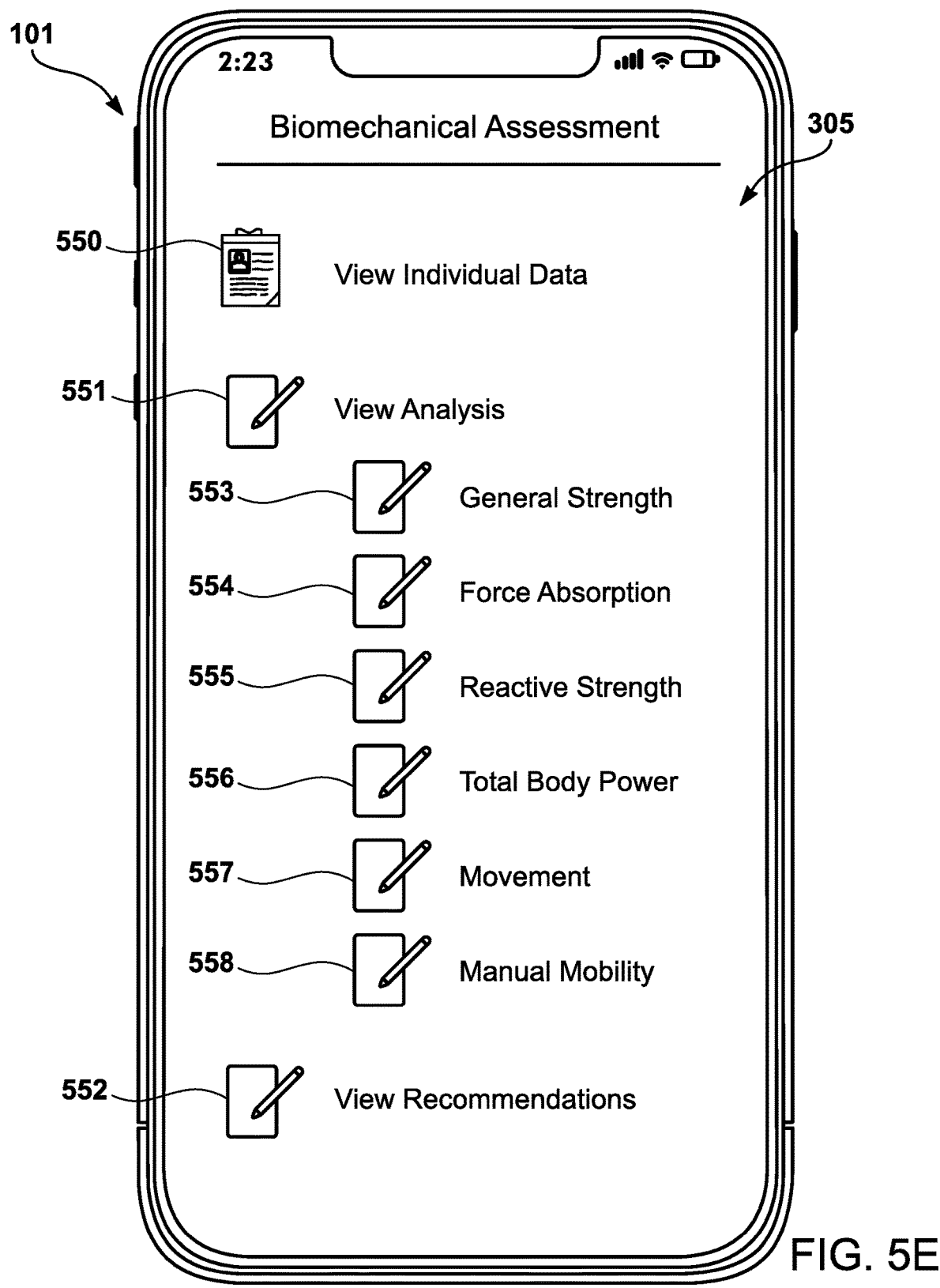
FIG. 5E illustrates the GUI rendering a biomechanical analysis display with various menu selections.

Moreover, the GUI 305 may display a biomechanical assessment upon a selection of the biomechanical assessment indicium 308. As an example, FIG. 5E illustrates the GUI 305 rendering a biomechanical assessment display with various menu selections. As examples, individual data indicium 550, analysis indicium 551, and recommendations indicium 552 may be displayed by the GUI 305. Furthermore, each indicium may have various sub-indicia. For example, the analysis indicium 551 may have a general strength sub-indicium 553, a force absorption sub-indicium 554, a reactive strength sub-indicium 555, a total body power sub-indicium 556, a movement sub-indicium 557, and a manual mobility sub-indicium 558. Accordingly, the second user 302 may select the various indicia and sub-indicia to obtain particular data pertaining to the movement performance of the first user 301. In one embodiment, such data includes a plurality of scores (e.g., numeric, relative (low, medium, high), etc.) corresponding to the various metrics. Furthermore, the recommendations indicium 552 may include various recommendations for exercises or modifications to the movements performed by the first user 301.

FIGS. 3A, 3B, and 5A-5E are directed to the instance whereby the first user 301 performs the baseline exercises/movements, followed by the actual sport-specific movements or other types of movements. In essence, the mobile computing device 101 is illustrated as allowing for a multi-user configuration: the first user 301 performs movements while the second user 302 guides the first user 301 based upon prompts/indications rendered by the mobile computing device 101.

Figure 6:
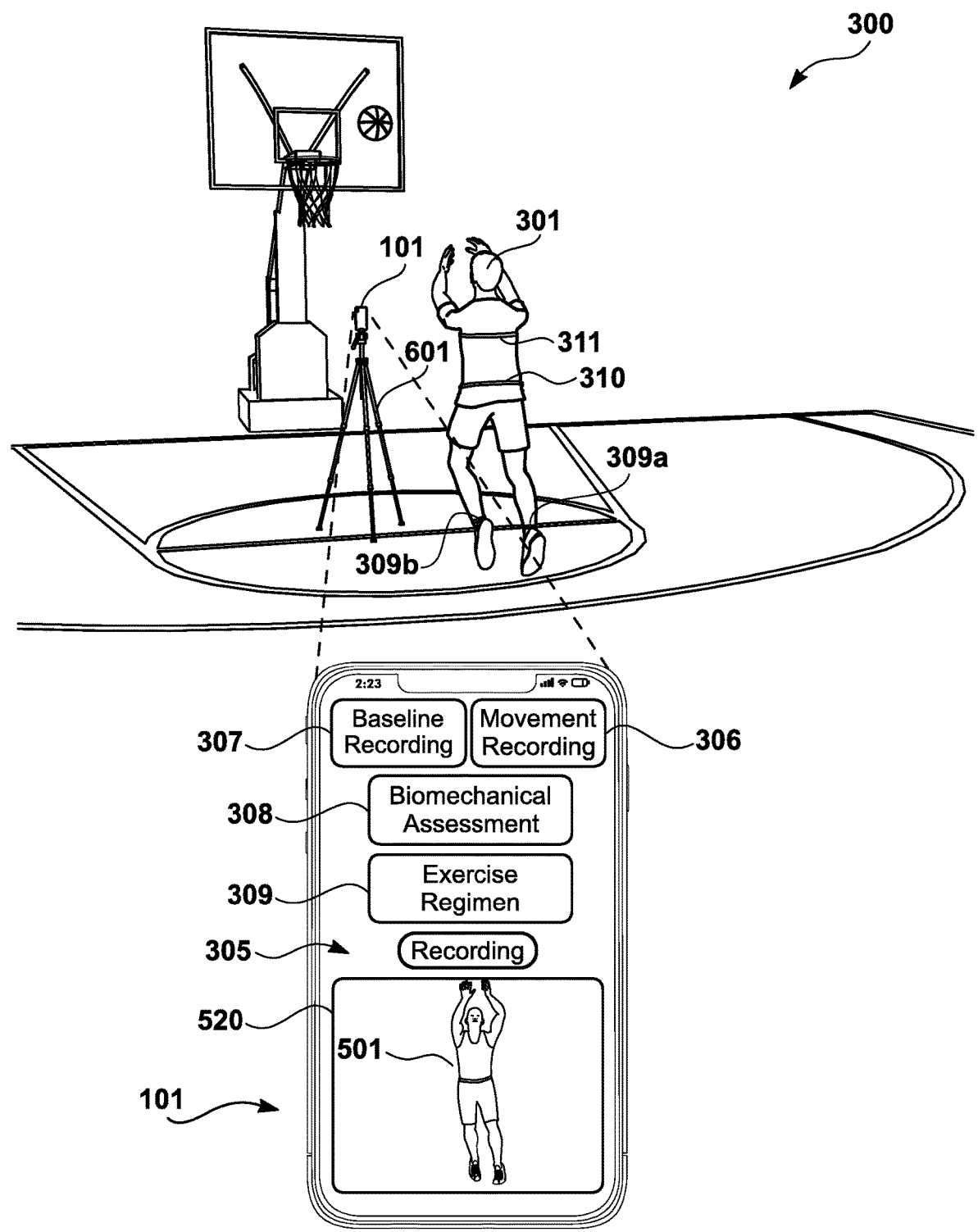
FIG. 6 illustrates an example of a single-user configuration in which the first user performs the movements, while concurrently viewing the mobile computing device.

In an alternative embodiment, a single-user configuration, rather than a multi-user configuration, may be utilized to implement the configurations provided for herein. As an example, FIG. 6 illustrates a single-user configuration in which the first user 301 performs the movements, while concurrently viewing the mobile computing device 101. As an example, the mobile computing device 101 may be positioned on a tripod 601 to allow the first user 301 to view the avatar 501 during performance of the movements. (Other types of devices (e.g., kickstands, straps, etc.) may be utilized instead. Alternatively, the first user 301 may hold or wear the mobile computing device 101 during the movements.)

Although the avatar 501 is illustrated as being rendered directly on the display screen of the mobile computing device 101, in an alternative embodiment, the avatar 501 may be rendered external to the mobile computing device 101. For example, an integrated holographic projector, or an external holographic projector in operable communication with the mobile computing device 101, may emit a hologram of the first user 301 as he or she performs the movements. As another example, an external display device (e.g., television, computer monitor, etc.) may be in operable communication with the mobile computing device 101, and render the movements of the first user 301.

In one embodiment, the avatar 501 may be generated from a skeletal body map that is determined from the real-world movements of the first user 301 based upon a computer vision process that is performed by the image capture device 254 in conjunction with the processor 201 and/or the processor 251. The accuracy of the measurements may be improved via the sensors 254. In essence, the skeletal body map may be transferred to the avatar 501 to allow for synchronized movement between the avatar 501 and the first user 301. In an alternative embodiment, the avatar 501 may be generated by obtaining a still, or dynamic, real-world image of the first user and generating corresponding anatomical structures for the avatar 501 for subsequent manipulation. The avatar 501 provides for clear articulation of the limbs/joints of the first user 301, which may not necessarily be emphasized from a visual cue perspective when using real-world video of the first user 301. Furthermore, the avatar 501 may be selected from a variety of computer-animated figures (e.g., cartoons, emoji, etc., such as favorite sports players of the first user 301). As another alternative, instead of the avatar 501, video of the first user 301 may be displayed. As yet another alternative, the avatar 501 may be utilized for the baseline movements, illustrated in FIGS. 3A and 3B, as opposed to the video/imagery of the first user 301.

Figure 7:
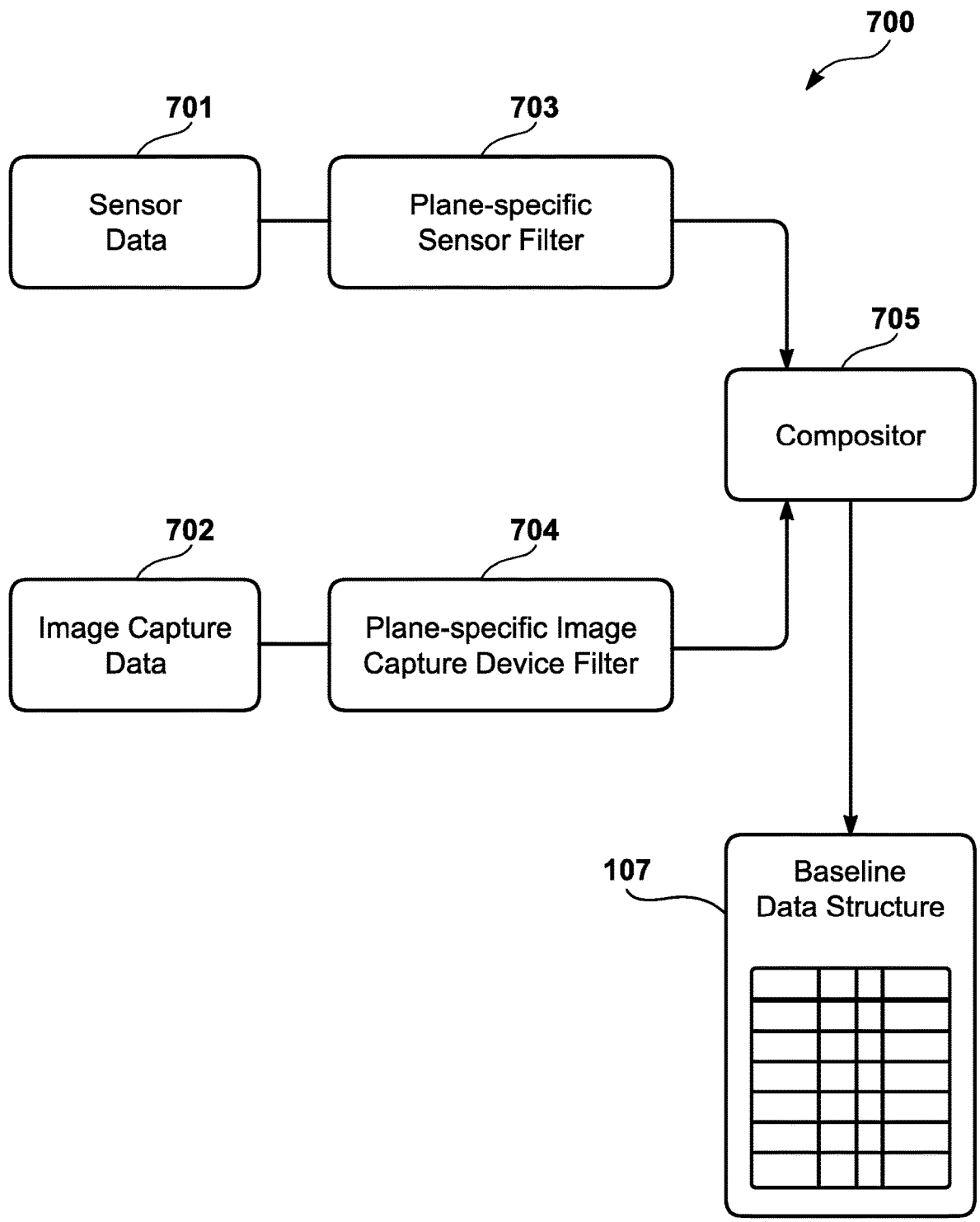
FIG. 7 illustrates a compositing process that may be utilized to generate the baseline data for the baseline data structure illustrated in FIG. 4.

FIG. 7 illustrates a compositing process 700 that may be utilized to generate the baseline data for the baseline data structure 107 illustrated in FIG. 4. In particular, the mobile computing device 101 and/or the server 102 may take the sensor data 701 and the image capture data 702 as captured from the first user 301 and perform filtering on that data to optimize data selection based on specific planes. For instance, in one embodiment, a plane-specific sensor filter 703 may filter the sensor data 701 to select only the sensor data that is most suitable for a particular plane (e.g., transverse plane 303) and the image capture data 702 that is most suitable for another plane (e.g., frontal plane 304). Accordingly, the compositing process 700 efficiently optimizes data selection based upon an optimal data source, and removes data redundancies by filtering out duplicative data that is less than optimal from that data source. For instance, at the completion of the filtering process, only sensor data pertaining to the hips is utilized from the transverse plane 303; the sensor data pertaining to gross motor motions may be filtered out since the image capture device 254 may capture that data in a more accurate manner. Conversely, only image data pertaining to the gross movements (e.g., knee flexion) is utilized from the frontal plane 304; the image data pertaining to the hips is filtered out since the sensor 253 may capture that data in a more accurate manner. In another embodiment, the overlapping data may be stored rather than filtered, but the optimal data may be utilized for the compositing process. After filtering, the plane-specific sensor filter 703 and the plane-specific image capture device filter 704 may send the remaining data to the compositor 705 that may composite the remaining data for storage as baseline data in the baseline data field 403 in the baseline data structure 107.

Figure 8:
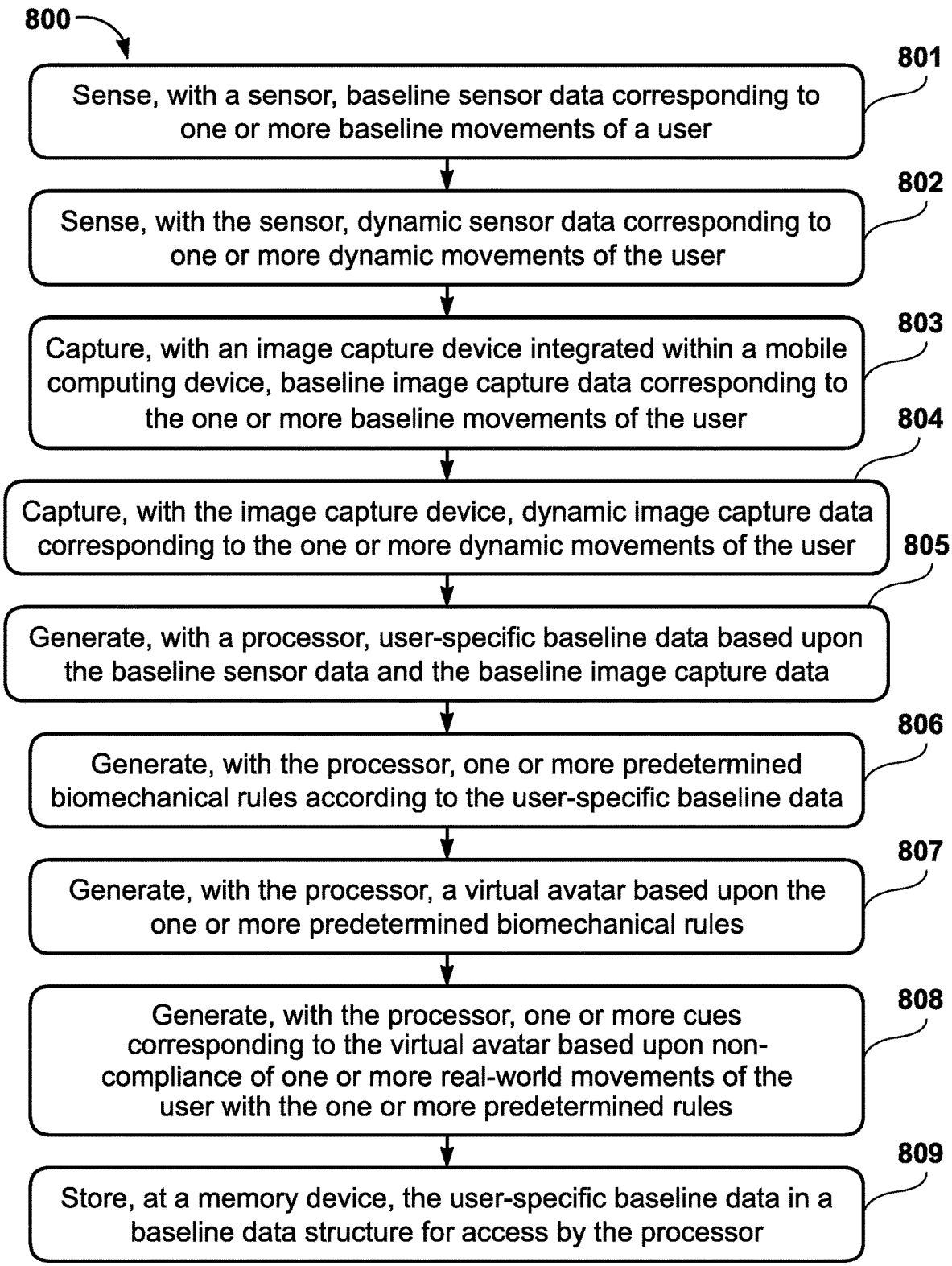
FIG. 8 illustrates a process that may be utilized to generate a virtual avatar based upon sensor data and imagery data to customize biofeedback for the first user.

FIG. 8 illustrates a process 800 that may be utilized to generate a virtual avatar based upon sensor data and imagery data to customize biofeedback to the first user 301. At a process block 801, the process 800 senses, with a sensor 253, baseline sensor data corresponding to one or more baseline movements of the first user 301. Furthermore, at a process block 802, the process 800 senses, with the sensor 253, dynamic sensor data corresponding to one or more dynamic movements of the first user 301. In addition, at a process block 803, the process 800 captures, with an image capture device 254 integrated within a mobile computing device 101, baseline image capture data corresponding to the one or more baseline movements of the first user 301. At a process block 804, the process 800 captures, with the image capture device 254, dynamic image capture data corresponding to the one or more dynamic movements of the first user 301. Additionally, at a process block 805, the process 800 generates, with the processor 201 or the processor 251, user-specific baseline data based upon the baseline sensor data and the baseline image capture data. Moreover, at a process block 806, the process 800 generates, with the processor 201 or the processor 251, one or more predetermined biomechanical rules according to the user-specific baseline data. At a process block 807, the process 800 generates, with the processor 201 or the processor 251, a virtual avatar 501 based upon the one or more predetermined biomechanical rules. Also, at a process block 808, the process 800 generate, with the processor 201 or the processor 251, one or more cues 510 corresponding to the virtual avatar 501 based upon non-compliance of one or more real-world movements of the first user 301 with the one or more predetermined rules. Finally, at a process block 809, the process 800 stores, at the memory device 202 or the memory device 252, the user-specific baseline data in a baseline data structure 107 for access by the processor 201 or the processor 251.

A computer is intended herein to include any device that has a specialized processor as described above. For example, a computer may be a personal computer ("PC"), laptop computer, set top box, cell phone, smartphone, tablet device, smart wearable device, portable media player, video player, etc. The configurations provided for herein may be implemented in various forms of computers.

It is understood that the apparatuses, systems, computer program products, and processes described herein may also be applied in other types of apparatuses, systems, computer program products, and processes. Those skilled in the art will appreciate that the various adaptations and modifications of the embodiments of the apparatuses described herein may be configured without departing from the scope and spirit of the present apparatuses, systems, computer program products, and processes. Therefore, it is to be understood that, within the scope of the appended claims, the present apparatuses, systems, computer program products, and processes may be practiced other than as specifically described herein.

I claim:

1. A system comprising:
a sensor configured to sense baseline sensor data corresponding to one or more baseline movements of a user and senses dynamic sensor data corresponding to one or more dynamic movements of the user, the dynamic sensor data being captured after the baseline sensor data;
an image capture device integrated within a mobile computing device, the image capture device configured to capture one baseline image capture data corresponding to the one or more baseline movements of the user and configured to capture dynamic image capture data corresponding to the one or more dynamic movements of the user, the dynamic image capture data being captured after the baseline image capture data, the mobile computing device being in operable communication with the sensor;
a processor that is programmed to generate user-specific baseline data based upon the baseline sensor data and the baseline image capture data, generate one or more predetermined biomechanical rules according to the user-specific baseline data, generate a virtual avatar based upon the one or more predetermined biomechanical rules, generate one or more cues corresponding to the virtual avatar based upon non-compliance of one or more real-world movements of the user with the one or more predetermined rules, filter the baseline sensor data according to an optimal sensor-specific plane that intersects the user during the one or more baseline movements, filter the baseline image capture data according to an optimal image capture device-specific plane that intersects the user during the one or more baseline movements, and composite the remaining data as the baseline data for generation of the virtual avatar, the one or more real-world movements being determined from the dynamic sensor data and the dynamic image capture data, the virtual avatar having virtual movements that are synchronized in real-time with the corresponding one or more real-world movements; and
a memory device configured to store the user-specific baseline data in a baseline data structure for access by the processor.

2. The system of claim 1, wherein the processor is further programmed to render the virtual avatar on a display device corresponding to the mobile computing device.

3. The system of claim 2, wherein the processor is further programmed to render a graphical user interface on the display device that provides a menu, the menu provide an indicium that activates recording of the one or more baseline movements and an indicium that activates recording of the one or more dynamic movements.

4. The system of claim 3, wherein the menu further comprises a biomechanical analysis indicium that generates access to a report of compliance of the user with the one or more predetermined biomechanical rules.

5. The system of claim 4, wherein the report includes one or more scores corresponding to performance metrics.

6. The system of claim 3, wherein the menu further comprises a biomechanical recommendation indicium that generates one or more recommendations for compliance with the one or more predetermined rules.

7. The system of claim 1, wherein the one or more cues are visual cues that visually indicate a biomechanical structure of the user that is non-compliant with the one or more predetermined rules.

8. The system of claim 1, wherein the one or more cues are auditory cues that indicate, via an auditory output, a biomechanical structure of the user that is non-compliant with the one or more predetermined rules.

9. The system of claim 1, wherein the mobile computing device is selected from the group consisting of: a smartphone, tablet device, smart glasses, and a smart watch.

10. The system of claim 1, wherein the one or more baseline movements correspond to one or more exercises that the processor analyzes to determine one or more ranges of motion particular to the user, wherein the one or more dynamic movements correspond to one or more sport-specific movements, the one or more exercises being distinct from the one or more sport-specific movements.

11. A computer program product comprising a non-transitory computer readable medium having a computer readable program stored thereon, wherein the computer readable program when executed on a computer causes the computer to:
sense, with a sensor, baseline sensor data corresponding to one or more baseline movements of a user;
sense, with the sensor, dynamic sensor data corresponding to one or more dynamic movements of the user, the dynamic sensor data being captured after the baseline sensor data;
capture, with an image capture device integrated within a mobile computing device, baseline image capture data corresponding to the one or more baseline movements of the user;
capture, with the image capture device, dynamic image capture data corresponding to the one or more dynamic movements of the user, the dynamic image capture data being captured after the baseline image capture data, the mobile computing device being in operable communication with the sensor;
generate, with a processor, user-specific baseline data based upon the baseline sensor data and the baseline image capture data;
generate, with the processor, one or more predetermined biomechanical rules according to the user-specific baseline data;
generate, with the processor, a virtual avatar based upon the one or more predetermined biomechanical rules;
generate, with the processor, one or more cues corresponding to the virtual avatar based upon non-compliance of one or more real-world movements of the user with the one or more predetermined rules, the one or more real-world movements being determined from the dynamic sensor data and the dynamic image capture data, the virtual avatar having virtual movements that are synchronized in real-time with the corresponding one or more real-world movements;
filter, with the processor, the baseline sensor data according to an optimal sensor-specific plane that intersects the user during the one or more baseline movements;

filter, with the processor, the baseline image capture data according to an optimal image capture device-specific plane that intersects the user during the one or more baseline movements;

composite, with the processor, the remaining data as the baseline data for generation of the virtual avatar; and store, at a memory device, the user-specific baseline data in a baseline data structure for access by the processor.

12. The computer program product of claim 11, wherein the computer is further caused to render the virtual avatar on a display device corresponding to the mobile computing device.

13. The computer program product of claim 12, wherein the computer is further caused to render, with the processor, a graphical user interface on the display device that provides a menu, the menu provide an indicium that activates recording of the one or more baseline movements and an indicium that activates recording of the one or more dynamic movements.

14. The computer program product of claim 13, wherein the menu further comprises a biomechanical analysis indicium that generates access to a report of compliance of the user with the one or more predetermined biomechanical rules.

15. The computer program product of claim 14, wherein the report includes one or more scores corresponding to performance metrics.

16. The computer program product of claim 13, wherein the menu further comprises a biomechanical recommendation indicium that generates one or more recommendations for compliance with the one or more predetermined rules.

17. The computer program product of claim 11, wherein the one or more cues are visual cues that visually indicate a biomechanical structure of the user that is non-compliant with the one or more predetermined rules.

18. The computer program product of claim 11, wherein the one or more cues are auditory cues that indicate, via an auditory output, a biomechanical structure of the user that is non-compliant with the one or more predetermined rules.

* * * * *